US00PP25512P3

(12) United States Plant Patent
Pavlich

(10) Patent No.: US PP25,512 P3
(45) Date of Patent: May 5, 2015

(54) ***BEGONIA* PLANT NAMED 'ENCHANTED EVENING'**

(50) Latin Name: ***Begonia* hybrid**
Varietal Denomination: Enchanted Evening

(71) Applicant: Terra Nova Nurseries, Inc., Canby, OR (US)

(72) Inventor: John C. Pavlich, East Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 98 days.

(21) Appl. No.: 13/987,226

(22) Filed: Jul. 12, 2013

(65) Prior Publication Data

US 2015/0020267 P1 Jan. 15, 2015

(51) Int. Cl.
*A01H 5/02* (2006.01)

(52) U.S. Cl.
USPC ..... Plt./343

(58) Field of Classification Search
CPC ..... A01H 5/0238
USPC ..... Plt./343
See application file for complete search history.

(56) References Cited

PUBLICATIONS

New Plants and Flowers, Dec. 6, 2012.*

* cited by examiner

*Primary Examiner* — June Hwu
*Assistant Examiner* — Keith Robinson
(74) *Attorney, Agent, or Firm* — Klarquist Sparkman, LLP

(57) ABSTRACT

A new and distinct form of *Begonia* plant characterized by attractive dark chocolate brown leaves with green veins, numerous large coral pink flowers, an upright habit when young, becoming decumbent with maturity, an extremely long bloom time, a caudiciform base, and excellent vigor.

1 Drawing Sheet

Botanical denomination: *Begonia* hybrid.
Variety designation: 'Enchanted Evening'.

BACKGROUND OF THE INVENTION

The present invention relates to a new and distinct cultivar of *Begonia*, of the family Begoniaceae, and given the cultivar name, 'Enchanted Evening'. The new cultivar originated from a cross between an unnamed, unpatented, seedling from a NONSTOP MOCCA Mix *Begonia*, an unpatented tuberous *Begonia*, as the seed parent and *Begonia boliviensis*, an unnamed, unpatented tuberous *Begonia*, as the pollen parent. This selection is uniquely characterized by:

1. attractive dark chocolate brown leaves with green veins,
2. numerous large coral pink flowers,
3. an upright habit when young, becoming decumbent with maturity,
4. an extremely long bloom time,
5. a caudiciform base, and
6. excellent vigor.

Compared to the seed parent, a NONSTOP MOCCA *Begonia*, the new cultivar has a larger habit with smaller and more numerous flowers that bloom over a much longer period.

Compared to the pollen parent, *Begonia boliviensis*, the new cultivar has larger, darker leaves, larger flowers that are coral pink rather than red, and longer bloom time.

Compared to the coral pink flowered *Begonia×hiemalis* types (unnamed, unpatented plants), the new cultivar has dark foliage with green veins rather than green leaves.

The new variety has been reproduced only by asexual propagation (leaf and stem cuttings and tissue culture). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a three month old plant of the new cultivar in 4 inch pot in a warm greenhouse in April in full bloom in Canby, Oreg.

FIG. 2 shows a two year old plant in full bloom in June in a 2 gallon container in Canby, Oreg.

DETAILED PLANT DESCRIPTION

The following is a detailed description of the new *Begonia* cultivar based on observations of 3-month-old specimens grown in 4 inch containers in a warm greenhouse in April in Canby, Oreg. The color descriptions are all based on The Royal Horticultural Society Colour Chart, 5$^{th}$ edition, 2007.

Plant:

*Type*.—Herbaceous, caudiciform perennial.
*Form*.—Upright when young, caulescent, becoming decumbent with maturity.
*Cold hardiness*.—USDA Zone 10.
*Size*.—Grows to 22 cm tall and 26 cm wide.
*Vigor*.—Excellent.
*Roots*.—Rooting initiates in two weeks, roots White NN155C in color.

Stem:

*Type*.—Upright in the first season, becoming decumbent with age.

*Size*.—Grows to 20 cm long and 1 mm wide (mature stems will grow to 50 cm long and 12 mm wide if left on the plant).

*Internodes*.—From 7 mm to 2 cm long.

*Surface*.—Glabrous.

*Color*.—Yellow Green 146A.

Leaf:

*Type*.—Simple.

*Arrangement*.—Alternate.

*Shape*.—Obliquely ovate to lanceolate.

*Leaf strength*.—Good.

*Margins*.—Serrate, slightly undulate, shallowly pinnately-lobed, with 1 to 5 lobes.

*Apex*.—Acuminate.

*Base*.—Oblique and truncate.

*Venation*.—Palmate, Green 136B topside, bottom side Green 138C.

*Blade size*.—Grows to 5.2 cm wide and 10.2 cm long.

*Surface texture*.—Pubescent on top and glabrous on bottom.

*Stipules*.—Deciduous, ovate, 7 mm long and 5 mm wide, apex acute and cuspidate, base clasping, entire, both sides pubescent, both sides Yellow Green 145C with base Greyed Purple 187B.

*Petiole description*.—Grows to 3.3 cm long and 3 mm wide, succulent, pubescent, Yellow Green 152B.

*Leaf color*.—Top side closest to Greyed Purple N186A with veins Green 136B; bottom side closest to Greyed Purple 187, but duller, with veins Green 138C.

Inflorescence:

*Type*.—Axillary, bisexual, cymose.

*Number of flowers per cyme*.—2 to 3.

*Peduncle description*.—Grows 7 cm long and 4 mm wide, sparsely pubescent, moderately strong, Yellow Green 152B tinted Greyed Orange 175A on top side in higher light; with 2 opposite, dehiscent petiolate leaf-bracts below each cyme, broadly ovate to orbicular, cupped and overlapping, each grow to 16 mm wide and 14 mm long, margins serrate and ciliate, tip obtuse, base clasping, both sides glabrous, both sides Yellow Green 152D lightly tinted Greyed Orange 175A.

*Pedicel description*.—Grow to 35 mm long, 1.5 mm wide, pubescent, medium strength Red 46B, except where shaded, Yellow Green 152B.

*Bloom period*.—Late winter to fall in Canby, Oreg.

Flower bud:

*Size*.—35 mm long and 27 mm wide prior to opening.

*Shape*.—Teardrop.

*Surface texture*.—Glabrous.

*Color*.—Red 55C on tepal area, Yellow Green 144A on ovary.

Flower:

*Type*.—Monoecious, bilaterally symmetrical.

*Pistillate flower*.—Grows to 20 mm deep and 92 mm wide overall; 5 fleshy tepals, grow to 45 mm long and 27 mm wide, obovate, tip obtuse to acute, base cuneate, margins entire, glabrous on both sides, top and bottom side closest to Red 55A; 1 pistil, 19 mm long overall, ovary to 20 mm wide and 11 mm deep, three winged, two equal and one longer, Yellow Green 145A tinted Greyed Red 179C on wings, style 3-branched, 8 mm deep and 12 mm wide overall, stigma 2-branched and twisted, stigma 5 mm deep and 5 mm wide overall, Yellow Orange 12A.

*Staminate flower*.—3 cm deep and 11 cm wide, glabrous and Red 55A on both sides; 2 outer tepals, 60 mm long and 41 mm wide, broadly elliptic, margin entire, tip obtuse, base obtuse; 2 inner tepals, 62 mm long and 29 mm wide, obovate, margin entire, tip obtuse, base attenuate; stamen many in a globular head 12 mm in long and 10 mm deep, filaments 3 mm to 4 mm long, Yellow 19B, anthers 1 mm long and Yellow Orange 21A, pollen Yellow 19A.

*Fragrance*.—None.

*Lastingness*.—A cyme blooms for about 2 weeks on the plant, flowers are self-cleaning.

Fruit and seed: None seen.

Diseases and pests: The new cultivar is typical to the genus. No known resistances to pests or diseases. No problems have been found in Canby, Oreg.

I claim:

1. A new and distinct form of *Begonia* plant as hereby illustrated and described.

* * * * *

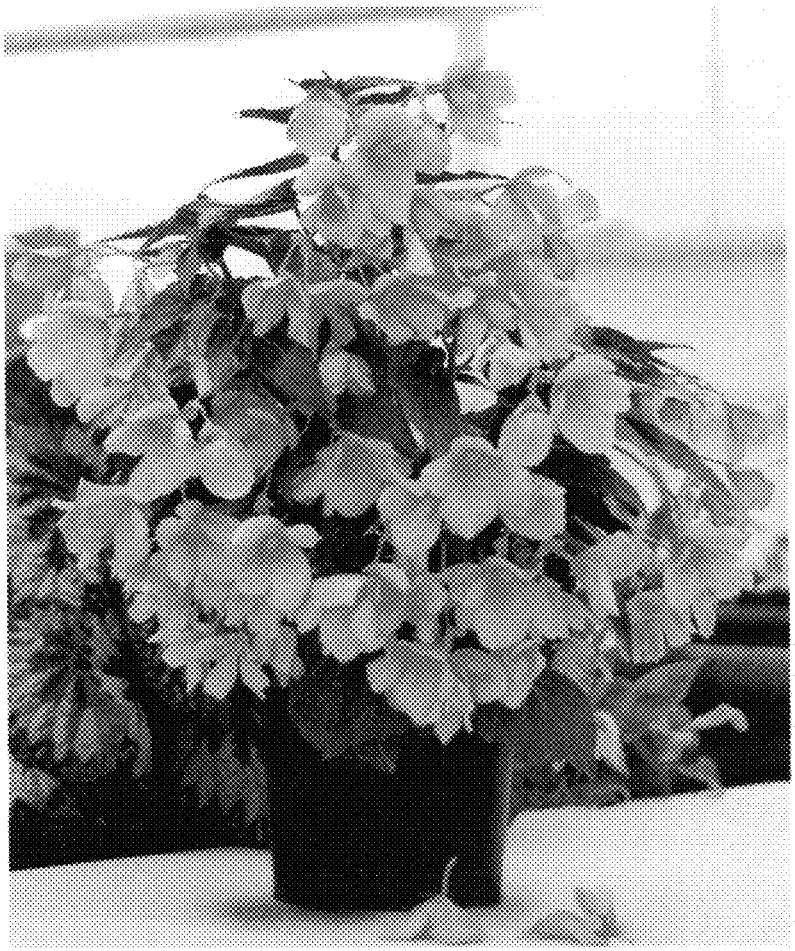

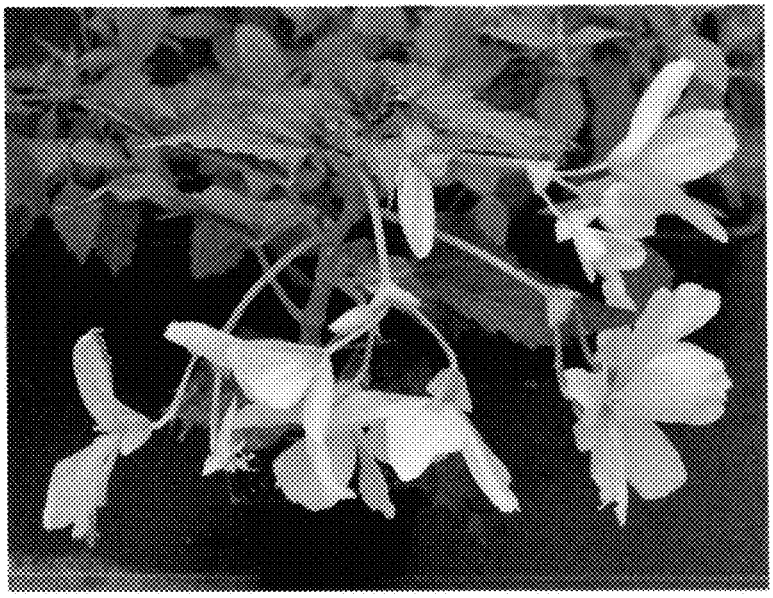
FIG. 1 above, FIG. 2 below